United States Patent [19]

Cox

[11] Patent Number: 5,419,220
[45] Date of Patent: May 30, 1995

[54] METHOD FOR MAKING A JAW FOR A BIOPSY FORCEPS

[76] Inventor: James E. Cox, 1951 St. Andrews Ct., Oxnard, Calif. 93030

[21] Appl. No.: 68,568

[22] Filed: May 28, 1993

[51] Int. Cl.⁶ .............................................. B21K 11/02
[52] U.S. Cl. ...................................... 76/104.1; 76/119; 128/751; 606/207
[58] Field of Search ................. 128/751; 606/205, 206, 606/207, 184, 160; 30/316; 76/101.1, 119, 104.1

[56] References Cited

U.S. PATENT DOCUMENTS

| | | | |
|---|---|---|---|
| 534,570 | 2/1895 | Norris | 30/316 |
| 1,515,000 | 11/1924 | Thompson | 30/316 X |
| 3,949,747 | 4/1976 | Hevesy | 606/184 X |
| 5,097,728 | 3/1992 | Cox et al. | 76/119 |
| 5,172,700 | 12/1992 | Bencini et al. | 128/751 |

FOREIGN PATENT DOCUMENTS 2671965  7/1992  France ................. 128/751

Primary Examiner—Michael H. Thaler
Attorney, Agent, or Firm—Donald D. Mon

[57] ABSTRACT

A method of making a jaw for a biopsy forceps in which a flat strip is formed with a sharpened edge and a tang with a pointed end. The strip is bent to form an open loop, and the tang is bent to extend upwardly into the loop.

3 Claims, 1 Drawing Sheet

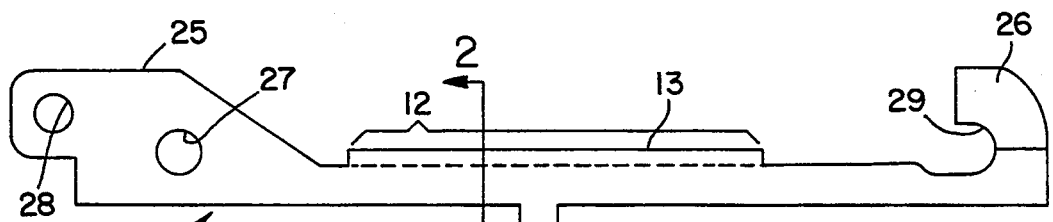
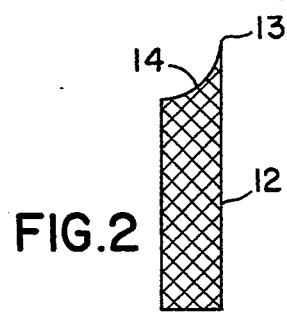
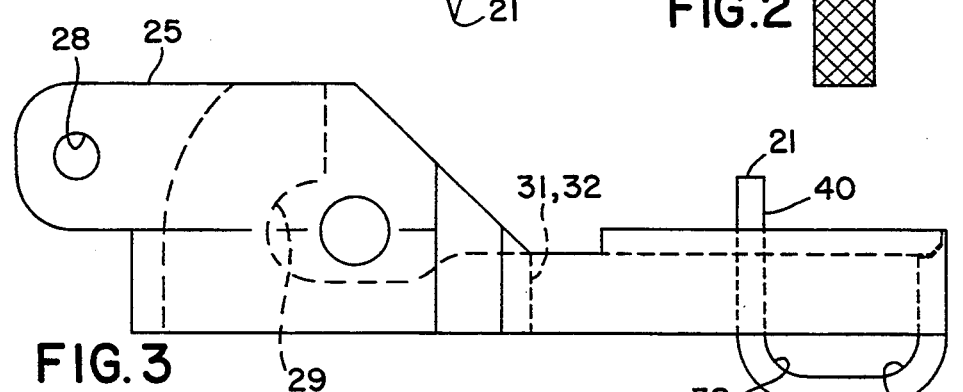
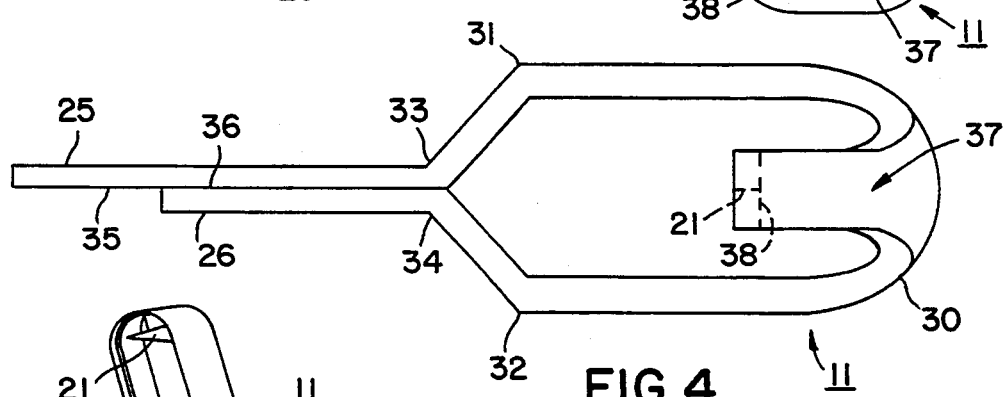
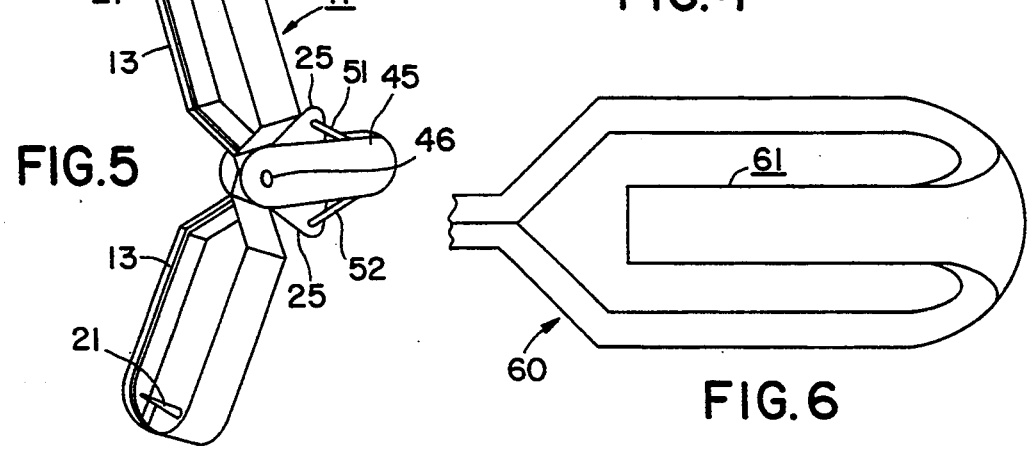

METHOD FOR MAKING A JAW FOR A BIOPSY FORCEPS

FIELD OF THE INVENTION

Biopsy forceps for excising tissue, especially in endoscopic procedures, and a method for making the jaws of the forceps.

BACKGROUND OF THE INVENTION

Biopsy forceps, especially those used in endoscopic procedures, must be small, readily manipulable, very sharp, and able reliably to retain the excised tissue while the forceps are being withdrawn.

Forceps for this purpose are well-known, although they generally fulfill their objectives to less than optimum satisfaction. One of their shortcomings is their cost. These forceps are very small, and are made to near-watchmaker precision. Forming their general shape is a simple task, but sharpening their edge, and providing sharp jaw edges which precisely abut one another is more difficult.

In Cox U.S. Pat. No. 5,097,728, issued Mar. 24, 1992, there is shown a method to make a small biopsy cup with a sharp edge. This edge is formed on a flat plate, and the plate is folded to form a cup in which the excised tissue is received. This device enjoys substantial utility, but has limitations which this instant invention proposes to overcome.

Another disadvantage of prior art biopsy forceps is the inherent limitation on how far their jaws can be opened. Because they are cup-shaped, their jaw opening is quite limited in order that a cut can be completed. If the cups are filled, then the jaws could not be fully closed to complete the cut. Also, if the jaws are opened after the cut is made, the specimen may be lost. The surgeon is unable to view the sample he has taken without assuming this risk. Too often, the closed forceps are withdrawn and when opened are found to be empty.

In its preferred embodiment this invention includes stabilizing means to stabilize the tissue while it is being severed, and has an open bottom so that the jaws cannot be overfilled. As a consequence, a very shallow cut can be made, which profoundly reduces the risk of perforation, and the jaws can be opened while still in the endoscopic system so that their content can be viewed through the endoscope without requiring removal of the forceps. In fact, it is even possible to take multiple specimens, because the stabilizing means tend to retain excised tissue even when the jaws are opened.

BRIEF DESCRIPTION OF THE INVENTION

Jaws for forceps according to this invention are formed from an initially flat strip. The strip has a sharpened edge portion, and is bent to form an open loop which is at least partially bounded by the sharp edge.

A tang is integral with the strip, and preferably has a sharp pointed end. The tang is bent to a U-shape to raise in the opening formed by this strip to provide a stabilizing strip.

In some applications, the tang may or may not be pointed, and is given only one 90 degree bend so as partially to occlude the opening, below the level of the sharpened edge.

Extensions can be included in the strip to provide a pivot aperture and a connection aperture for mounting the jaws to manipulation means and connecting the jaws to manipulating wires.

According to a preferred but optional feature of the invention, the extensions are spot welded together to form the jaw as a rigid structure.

To form the forceps, pivot means join the jaws together at the pivot apertures of the two jaws. The pivot means is mounted to a sheath, and two manipulation wires in the sheath are respectively connected to the apertures for the wires. Then, using a typical three finger loop 9rip, the jaws can be opened and closed.

The above and other features of this invention will be fully understood from the following detailed description and the accompanying drawings, in which:

BRIEF DESCRIPTION OF THE DRAWINGS

FIG. 1 is a plan view of a flat strip prepared to be formed into a forceps jaw according to this invention;

FIG. 2 is a cross section taken at line 2—2 in FIG. 1

FIG. 3 is a side view of a completed forceps jaw according to the invention;

FIG. 4 is a bottom view of FIG. 3;

FIG. 5 shows a pair of jaws according to FIG. 3 mounted to manipulation means to form a biopsy forceps; and FIG. 6 shows another embodiment of a jaw according to the invention.

DETAILED DESCRIPTION OF THE INVENTION

A flat strip 10 is shown in FIG. 1. It is shaped and later bent to form a forceps jaw 11 as shown in FIGS. 3-5.

Strip 10 includes a loop portion 12 which has a sharpened edge 13 as shown in FIG. 2. This sharpened edge is most advantageously formed by a chemical etching process which etches away some of the material to leave face 14 between side surfaces 15 and 16. The strip is preferably made of stainless steel, and is etched by chemical means to the edge shape shown in FIG. 1. Should different materials be used, other means to form the edge may be used instead. An etch-forming process is to be preferred, because it can be done as part of a process for making the strip as shown in FIG. 1. In fact, the strip 10 can be entirely formed by an etching process, and a plurality of these can be formed from a single sheet of material at the same time using masking etching techniques.

Despite the small sizes, it is possible to make the strip with stamping or machining processes, and to sharpen the edge by honing it. However, etching processes are very accurate and much less expensive than mechanical processes for making these small parts.

A tang 20 is formed integrally with the strip, extending normally to the band. It terminates at a sharp point 21.

Flanges 25 and 26 are formed as integral extensions of the band. Flange 25 has a pivot aperture 27 and an attachment aperture 28. Flange 26 has a cut-out clearance portion 29. The flanges are flat.

To form the jaw, the band is bent to form a bight 30 and bends 31 and 32. These bends are beyond the sharp edge. The sharp edge does not necessarily extend entirely around the loop, and usually will not, although it can.

Second bends 33 and 34 bring surfaces 35 and 36 into contiguity, and they can be spotwelded together, or joined by any other suitable means.

The tang is formed into a U-shaped structure with a first and a second right angle bend 37, 38, so that the pointed end rises through the loop and extends above it as a spear 40. These bends may be formed at any convenient time in the assembly of the jaw.

The point preferably rises above the cutting edge so that it makes an early contact with tissue to be excised, although this is optional.

To form the forceps, and assemble it to manipulation means, a sheath extension 45 mounts a pivot pin 46 which passes through the pivot apertures 27. The jaws are now mounted to be pivoted toward and away from each other, so that the cutting edges abut when the forceps are fully closed. While they were closing, the spears had engaged the tissue, and held it inside the loop so the edges can assuredly have made shallow cuts. The length 50 of the tang between the bends 37 and 38 will be different for the two jaws so that there will be a side clearance of perhaps 0.005 inches between the spears when the jaws are closed. It is not desired for the spears to interfere with each other, or for there to be a shearing action between them. In fact, when the jaws are closed, they overlap. While the spears are shown overlapping, this also is optional. They need not extend above the sharpened edge for some applications.

Wires 51, 52 are connected to the flanges 25 of the two jaws, so as to open and close the jaws. A conventional three loop handle (not shown) can be attached to the sheath and to the wires for manipulation purposes.

This set of jaws can be opened to about 170 degrees as shown in FIG. 5. This provides good visibility for the surgeon, and he can make a shallow cut. The stability spears secure the tissue against escape from the loop.

It is an advantage of this invention that the jaws do not form a fully closed cup. Instead there is an open region to pass tissue and avoid overpacking. In the embodiment of FIGS. 3 and 4, the tang partially occludes the opening and a spear rises into the opening.

FIG. 6 shows a jaw 60 generally the same as the jaws in FIGS. 3 and 4, except that the tang 61 does not have a sharp point and is not turned upwardly. Instead it extends across the opening, to occlude it more completely. The advantages of the spear are forfeited, and the loop is more closed, but for some applications this may be preferred, and is still within the scope of the invention.

In use, after a cut is made, the surgeon can open the forceps to be certain he has a specimen, and that it is a specimen he wants to have, without the risk of losing it, while the forceps is still inside the endoscope system. At least one of the spears will hold the specimen. Also, it is possible to take a second specimen, because usually the excised one will be retained in one of the jaws, and there is capacity for a second one, because the bottoms of the loops are open.

This invention is not to be limited by the embodiments shown in the drawings and described in the description, which are given by way of example and not of limitation, but only in accordance with the scope of the appended claims.

I claim:

1. A method for making a jaw for a biopsy forceps, comprising:
    forming a flat strip with a sharpened edge and a tang;
    bending said strip to form an open loop at least partially bounded by said sharpened edge; and
    bending said tang so as at least partially to occlude the open loop, bending said tang additionally to extend upwardly into said open loop, said tang being formed with a pointed end.
2. A method according to claim 1 in which said pointed end projects above said sharpened edge.
3. A method according to claim 1 in which said sharpened edge is formed by an etching process.

* * * * *

UNITED STATES PATENT AND TRADEMARK OFFICE
CERTIFICATE OF CORRECTION

PATENT NO. : 5,419,220
DATED : May 30, 1995
INVENTOR(S) : JAMES E. COX

It is certified that error appears in the above-indentified patent and that said Letters Patent is hereby corrected as shown below:

Title page, column 1, item [54], "METHOD FOR MAKING A JAW FOR A BIOPSY FORCEPS" should be --METHOD FOR MAKING A JAW FOR BIOPSY FORCEPS--

Title page, column 2, line just preceding item [57], after "Attorney, Agent, or Firm," delete "Donald D. Mon" and insert therefor --Workman, Nydegger & Seeley--
    Title page, item [57], line 2, "a biopsy forceps" should be --biopsy forceps--
    Column 2, line 11, "9rip" should be --grip--
    Column 2, line 19, after "FIG. 1" insert --;--
    Column 4, line 14, "forceps is" should be --forceps are--
    Column 4, line 26, "for a biopsy forceps" should be --for biopsy forceps--

Signed and Sealed this

Eighteenth Day of June, 1996

Attest:

BRUCE LEHMAN

Attesting Officer     *Commissioner of Patents and Trademarks*